(12) United States Patent
Nakayama et al.

(10) Patent No.: US 9,206,441 B2
(45) Date of Patent: Dec. 8, 2015

(54) METHOD FOR PRODUCING CELL HAVING NUCLEIC ACID INTRODUCED THEREIN

(71) Applicants: NATIONAL CEREBRAL AND CARDIOVASCULAR CENTER, Suita-shi, Osaka (JP); BRIDGESTONE CORPORATION, Chuo-ku, Tokyo (JP)

(72) Inventors: Yasuhide Nakayama, Toyonaka (JP); Ryosuke Iwai, Kobe (JP); Yasushi Nemoto, Yokohama (JP)

(73) Assignees: NATIONAL CEREBRAL AND CARDIOVASCULAR CENTER, Osaka (JP); BRIDGESTONE CORPORATION, Tokyo (JP)

( * ) Notice: Subject to any disclaimer, the term of this patent is extended or adjusted under 35 U.S.C. 154(b) by 0 days.

(21) Appl. No.: 14/369,526

(22) PCT Filed: Dec. 26, 2012

(86) PCT No.: PCT/JP2012/083611
§ 371 (c)(1),
(2) Date: Jun. 27, 2014

(87) PCT Pub. No.: WO2013/099924
PCT Pub. Date: Jul. 4, 2013

(65) Prior Publication Data
US 2015/0011005 A1  Jan. 8, 2015

(30) Foreign Application Priority Data
Dec. 28, 2011 (JP) .................. 2011-287594

(51) Int. Cl.
*C12N 15/87* (2006.01)
*C12N 15/09* (2006.01)
*B82Y 5/00* (2011.01)

(52) U.S. Cl.
CPC ............... *C12N 15/87* (2013.01); *C12N 15/09* (2013.01); *B82Y 5/00* (2013.01)

(58) Field of Classification Search
None
See application file for complete search history.

(56) References Cited

FOREIGN PATENT DOCUMENTS

| | | |
|---|---|---|
| JP | 2008-194003 A | 8/2008 |
| JP | 2008-195681 A | 8/2008 |
| JP | 2009-275001 A | 11/2009 |
| JP | 2009-275002 A | 11/2009 |
| JP | 2010-136631 A | 6/2010 |
| JP | 2010-136632 A | 6/2010 |
| JP | 4475847 B2 | 6/2010 |
| JP | 2010-273565 A | 12/2010 |
| JP | 2011-072257 A | 4/2011 |
| WO | 2004/078961 A1 | 9/2004 |

OTHER PUBLICATIONS

Li, et al. (1999) "Stimuli-Responsive Behavior of N,N-Dimethylaminoethyl Methacrylate Polymers and Their Hydrogels", Chapter 18 of In Field Responsive Polymers; Khan, I., et al, ACS Symposium Series, Published by the American Chemical Society, Washington, DC., USA, 1999, pp. 266-276.*
English translation of Ryosuke Iwai, et al., "Kan'onsei Cation-sei Homopolymer no Mukaishi Muyobai Hikari Jugo ni yoru Gosei to Kyuchaku Idenshi Donyu", ("Synthesis of temperature responsive cationic homopolymer by photopolymerization without an initiator and a solvent and introduction of gene absorbed to the substrate"), The Japanese Journal of Artificial Organs, Oct. 25, 2011, pp. 82, vol. 40, No. 2.
Extended European Search Report issued Jun. 11, 2015 in European Patent Application No. 12863681.8.
Ryosuke Iwai, et al., "Deposition Gene Transfection Using Bioconjugates of DNA and Thermoresponsive Cationic Homopolymer", Bioconjugate Chem., 2012, vol. 23, pp. 751.757, XP-002740190.
Ryosuke Iwai, et al., "Enhanced Transfection Efficiency of Poly(N,N-dimethylaminoethyl methacrylate)-Based Deposition Transfection by Combination with Tris(hydroxymethyl)aminomethane", Bioconjugate Chem., 2013, vol. 24, pp. 15-166, XP-002740191.
Ryosuke Iwai, et al., "Kan'onsei Cation-sei Homopolymer no Mukaishi Muyobai Hikari Jugo ni yoru Gosei to Kyuchaku Idenshi Donyu", The Japanese Journal of Artificial Organs, Oct. 25, 2011, pp. 82, vol. 40, No. 2.
Hiroshi Iwasaki, et al., "Preparation of 2-(Dimethylamino) ethyl Methacrylate-Styrene Copolymers and Temperature Responsiveness of Their Copolymer Solutions", Japanese Journal of Polymer Science and Technology, Sep. 25, 2011, pp. 623-630, vol. 68, No. 9.

* cited by examiner

*Primary Examiner* — Robert M Kelly
(74) *Attorney, Agent, or Firm* — Sughrue Mion, PLLC

(57) ABSTRACT

A method for producing a cell having nucleic acid introduced therein and having low cytotoxicity is useful in primary cells and slowly dividing cells, for which nucleic acid introduction is difficult with conventional techniques. A method for introducing nucleic acid into a cell includes the steps of mixing a nucleic acid with a temperature sensitive material at a temperature lower than the cloud point of the temperature sensitive material, the temperature sensitive material being formed by adding 2-amino-2-hydroxymethyl-1,3-propanediol to a temperature-sensitive polymer material having 2-N,N-dimethylaminoethyl methacrylate and/or a derivative thereof as the main polymer component, flow coating a culture vessel with the resulting mixed liquid, and culturing a cell suspension provided to the culture vessel at a temperature higher than the cloud point.

3 Claims, 7 Drawing Sheets

Example 2 — Small Diffusion

Comparative Example 3 — Large Diffusion

METHOD FOR PRODUCING CELL HAVING NUCLEIC ACID INTRODUCED THEREIN

CROSS REFERENCE TO RELATED APPLICATIONS

This application is a National Stage of International Application No. PCT/JP2012/083611, filed Dec. 26, 2012, claiming priority from Japanese Patent Application No. 2011-287594, the contents of all of which are incorporated herein by reference in their entirety.

TECHNICAL FIELD

The present invention relates to a method for producing a cell having nucleic acid introduced therein, and in particular relates to a method for producing a cell having nucleic acid introduced therein using temperature-sensitive polymer material of which the main polymer component is 2-N,N-dimethylaminoethyl methacrylate and/or a derivative thereof.

BACKGROUND ART

An N-isopropylacrylamide polymer and a 2-(N,N-dimethylaminoethyl) methacrylate polymer are widely known as temperature-sensitive polymers exhibiting temperature sensitivity such that the polymers are hydrophilic at a lower temperature than the cloud point and hydrophobic at a temperature higher than the cloud point (Patent Literature 1 to 5).

As described in Patent Literature 1, poly(N-isopropylacrylamide) is hydrophobic near 37° C. and hydrophilic near 25° C., and these properties can be used to remove cultured cells from a culture dish. Cells adhere to a hydrophobic surface, and therefore when poly(N-isopropylacrylamide) is hydrophobic at 37° C., cells can be cultured on a culture dish to which poly(N-isopropylacrylamide) has been adhered. Upon the poly(N-isopropylacrylamide) becoming hydrophilic at 25° C., the cultured cells can be removed from the culture dish. Using this phenomenon, a cell sheet can be peeled off from the culture dish and collected.

In recent years, as the molecular genetic cause of human disease has become clear, more and more emphasis has been placed on gene therapy research. The purpose of gene therapy is to express DNA at the target site. What is crucial is how to cause the DNA to reach the target site, how to efficiently introduce the DNA into the target site, and how to express the DNA functionally at the site. As a vector for introducing foreign DNA, many viruses are modified to carry therapeutic genes and are used in clinical trials on humans for gene therapy. Such viruses include a retrovirus, adenovirus, adeno-associated virus, lentivirus, Sendai virus, and herpesvirus. The risk of infection or an immune response, however, still remains.

Patent Literature 3 discloses a vector with a branch structure, in which a branched chain extends radially with an aromatic ring such as benzene as the nucleus and discloses how this vector can condense DNA at a high density to form a small nucleic acid complex molecule for efficient gene transfer to a cell.

Patent Literature 2 discloses a gene transfer agent that uses the temperature sensitivity of poly[2-(N,N-dimethylaminoethyl) methacrylate]. A compound having three or more N,N-dialkyldithiocarbamylmethyl groups in the same molecule is used as an iniferter, and the gene transfer agent is composed of a star polymer formed by light irradiation living polymerization of 2-N,N-dimethylaminoethyl methacrylate and/or a derivative thereof with the iniferter. In this gene transfer agent, the 2-N,N-dimethylaminoethyl methacrylate and/or derivative thereof that forms the branched chain is slightly cationic. Therefore, the cationic 2-N,N-dimethylaminoethyl methacrylate unit contributes to bonding with the nucleic acid, increasing the amount of nucleic acid supported by the gene transfer agent. Furthermore, in this gene transfer agent, the branched chain is sensitive to temperature, and by increasing the temperature, the gene transfer agent becomes hydrophobic.

Patent Literature 5 discloses a gene transfer agent that can support more nucleic acid. A compound having three or more N,N-dialkyldithiocarbamylmethyl groups in the same molecule is used as an iniferter, and the gene transfer agent is formed by light irradiation living polymerization of 2-N,N-dimethylaminoethyl methacrylate and/or a derivative thereof with the iniferter.

In the gene transfer agent disclosed in Patent Literature 5, the 2-N,N-dimethylaminoethyl methacrylate and/or derivative thereof that forms the branched chain is slightly cationic. Therefore, the cationic 2-N,N-dimethylaminoethyl methacrylate unit contributes to bonding with the nucleic acid, increasing the amount of supported nucleic acid. Furthermore, since the branched chain is sensitive to temperature, the gene transfer agent can be made hydrophobic by adjusting the temperature.

For both of the polymers N-isopropylacrylamide and 2-(N,N-dimethylaminoethyl) methacrylate, the LCST (cloud point) is near 32° C. in an aqueous solution. Using temperature sensitive characteristics whereby these polymers are hydrophobic at the body temperature range of mammals and hydrophilic at room temperature, these polymers are used in the fields of drug delivery systems (DDS) and cell culturing. Due to the kinetic energy of polymer side chains and the affinity with water molecules of the side chain molecular group, these temperature sensitive characteristics manifest themselves by causing transfer between a globular structure and a coiled structure near 30° C.

The gene transfer agent disclosed in Patent Literature 3 has the properties of being hydrophilic at a temperature lower than a predetermined temperature (T) and hydrophobic at a temperature higher than the predetermined temperature (T). Patent Literature 4 discloses a culture vessel that, using these properties, has this gene transfer agent adhered to the inner surface of the vessel. In Patent Literature 4, the hydrophobic property of the gene transfer agent can be used for the gene transfer agent to adhere to the inner surface of the vessel over an extended period of time.

Reverse transfection is a technique used in gene transfer to adherent cells. The culture dish is coated in advance with nucleic acid complexes or the like, and genes are introduced from the side of the adhered base material using extended release of nucleic acid from the coating layer and incorporation by cells. This technique constitutes a pair with regular transfection, in which nucleic acid complexes are dispersed/dissolved in a culture medium and are incorporated into cells from the culture medium.

CITATION LIST

Patent Literature

PTL 1: JP 4475847 B2
PTL 2: JP 2010-136631 A
PTL 3: JP 2008-195681 A
PTL 4: JP 2008-194003 A
PTL 5: JP 2011-72257 A

SUMMARY OF INVENTION

Technical Problem

1) N-isopropylacrylamide and poly[2-(N,N-dimethylaminoethyl) methacrylate], which are known as temperature sensitive polymers, have an LCST of approximately 32° C., and in a cell culturing environment (generally in an incubator adjusted to a temperature of 37° C.), express a hydrophobic property, localizing on the bottom of a culture dish and forming a coating layer. However, operations to coat an actual culture dish, to seed cells, and the like are performed in a clean bench that is maintained sterile (in a safety cabinet when performing a biohazard experiment at a containment level of P2 or higher). Even if a person of ordinary skill in the art versed in these operations works rapidly, the bottom of the culture dish temporarily reaches a temperature at or near room temperature. In particular, in a 24-well or greater porous culture dish or the like, operations take a longer time, making it easy for the culture dish to cool to near room temperature.

2) In order to stably maintain the temperature within the cell incubator at 37° C., the environmental temperature of the laboratory should be set, insofar as possible, to a different temperature than 37° C., for example to a low temperature of approximately 25° C. Since the coating layer is exposed to this environmental temperature, the hydrophobized layer becomes a lower temperature than the LCST and is eluted, thus nullifying the state and conditions for reverse transfection.

3) One theory holds that possibly due to a phenomenon whereby receptors and the like on the cell surface orient towards the surface of the adhered base material (i.e. a capping phenomenon), gene transfer is more efficient with reverse transfection than with regular transfection from the perspectives of the amount of nucleic acid used, the amount expressed, and the like. For example, a nucleic acid delivery technique using gelatin gel material, degradable resin material, or the like is a technique to release nucleic acid gradually along with degradation of the material in which nucleic acid is embedded and mixed, thereby providing nucleic acid to the adherent cell from the adhesive surface (bottom). There is a group that appreciates this usefulness and specializes in researching this technique. For reverse transfection using a temperature sensitive polymer, another technique being studied directly fixes a temperature sensitive polymer to a culture dish using radiation graft polymerization, so that the coating layer does not peel off. These techniques require that a support layer be fixed to the culture dish in advance during a complicated coating operation, and the support layer needs to be sterilized. Therefore, these techniques cannot be followed in experiments in which researchers each use a nucleic acid that is the target for their own culture dish.

4) With conventional techniques, polymer material (particle size of approximately 250 nm or less) in a culture medium that includes nucleic acid and the polymer material is sometimes incorporated into cells, causing cytotoxicity.

It is an object of the present invention to provide a method for producing a cell having nucleic acid introduced therein and having low cytotoxicity, the method being useful in primary cells and slowly dividing cells, for which nucleic acid introduction is difficult with conventional techniques.

Solution to Problem

A method according to the present invention for producing a cell having nucleic acid introduced therein includes the steps of: producing a gene transfer composition by mixing a nucleic acid with an aqueous solution of a temperature sensitive composition at a temperature lower than a cloud point of the temperature sensitive composition, the temperature sensitive composition being formed by adding 2-amino-2-hydroxymethyl-1,3-propanediol to a temperature-sensitive polymer material having 2-N,N-dimethylaminoethyl methacrylate and/or a derivative thereof as a main polymer component; adhering the gene transfer composition to a culture vessel; and culturing a cell suspension provided to the culture vessel at a temperature higher than the cloud point.

The aqueous solution of the temperature sensitive composition is preferably prepared by adding an aqueous solution of 2-amino-2-hydroxymethyl-1,3-propanediol to an aqueous solution of the temperature-sensitive polymer material.

The step of drying the temperature sensitive composition is preferably included between the step of adhering and the step of culturing.

The cloud point of the temperature sensitive composition is preferably from 10° C. to 25° C.

The "cloud point" of the temperature sensitive composition in the context of the present invention does not strictly refer to "a certain temperature such that the temperature sensitive material dissolves in water at less than that temperature but becomes insoluble and forms a hydrophobic agglomeration at that temperature or higher, yielding an aqueous suspension". It is difficult to measure the "cloud point" strictly, due to human-induced factors that affect the measurement value such as the speed of cooling/heating of the aqueous solution of the temperature sensitive composition, the size and heat-transfer efficiency of the container in which the aqueous solution is placed, the density of the temperature sensitive composition, and the like. In the context of the present invention, this difficulty is taken into consideration, and accordingly, the cloud point may also refer to a predetermined temperature such that when a temperature sensitive composition caused to be an insoluble agglomeration at 37° C. is set to less than the predetermined temperature, it takes several minutes or more for the temperature sensitive composition to become soluble again.

The molecular weight of the polymer material is preferably from 5,000 to 500,000.

Advantageous Effect of Invention

The cloud point of a temperature sensitive composition in which 2-amino-2-hydroxymethyl-1,3-propanediol is added to a temperature-sensitive polymer material having 2-N,N-dimethylaminoethyl methacrylate (DMAEM) and/or a derivative thereof as the main polymer component (referred to below simply as a "temperature-sensitive polymer material") is lower than the cloud point of the polymer material. As the added amount of 2-amino-2-hydroxymethyl-1,3-propanediol increases, the cloud point of the temperature sensitive composition is further reduced. Therefore, by adjusting the added amount, the cloud point of the temperature sensitive composition can be freely adjusted.

By spreading a gene transfer composition, formed by mixing the temperature sensitive composition with nucleic acid, on a culture vessel and exposing the culture vessel to a higher temperature than the cloud point, the spread liquid becomes a gel, forming a coating layer. By culturing a cell suspension provided to the culture vessel at a temperature higher than the cloud point, cells adhere to the coating layer, and the nucleic acid in the coating layer is incorporated into the cells.

In the method of the present invention, the coating layer in the culture vessel is not removed or eluted even if, during work in a clean bench, the coating layer achieves equilibrium with room temperature, and genes can be provided to adherent cells strictly from only the side of the adhered base material. According to the method of the present invention, transfection (provision of nucleic acid complexes from the culture medium side) can be performed stably to primary cells, which might preferentially incorporate matter from the adhesive surface due to the capping phenomenon.

In the method of the present invention, polymer material is fixed to a culture vessel. As a result, incorporation of the polymer material into cells is prevented or suppressed, thus reducing cytotoxicity.

In the method of the present invention, polymer material constituting the culture medium is fixed to the culture vessel. Therefore, the nucleic acid introduction material has excellent adhesiveness and long-term stability. Excellent gene transfer activity can thus be maintained over a long period of time.

BRIEF DESCRIPTION OF DRAWINGS

The present invention will be further described below with reference to the accompanying drawings, wherein.

DESCRIPTION OF EMBODIMENTS

Figure 1:
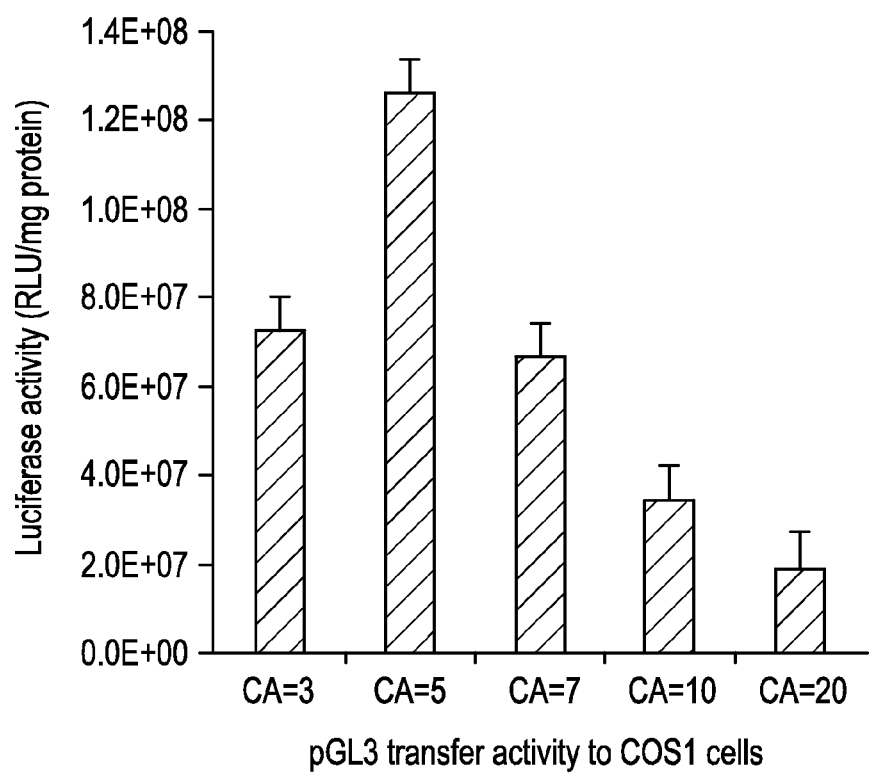
FIG. 1 is a graph illustrating gene transfer activity in Example 1.

The following describes an embodiment of the present invention in detail.

A method according to the present invention includes the steps of: producing a gene transfer composition by mixing a nucleic acid with a temperature sensitive composition at a temperature lower than a cloud point of the temperature sensitive composition, the temperature sensitive composition being formed by adding 2-amino-2-hydroxymethyl-1,3-propanediol to a temperature-sensitive polymer material having 2-N,N-dimethylaminoethyl methacrylate and/or a derivative thereof as a main polymer component; adhering the gene transfer composition to a culture vessel; and culturing a cell suspension provided to the culture vessel at a temperature higher than the cloud point. The step of drying the gene transfer composition may be performed between the step of adhering and the step of culturing.

A method according to an aspect of the present invention includes the steps of: preparing a mixed liquid by mixing a nucleic acid with a temperature sensitive composition at a temperature lower than a cloud point of the temperature sensitive composition, the temperature sensitive composition being formed by adding 2-amino-2-hydroxymethyl-1,3-propanediol to an aqueous solution of a temperature-sensitive polymer material having 2-N,N-dimethylaminoethyl methacrylate and/or a derivative thereof as a main polymer component; adhering the mixed liquid to the inner surface of a culture vessel to form a coating layer; and after drying the coating layer as necessary, culturing a cell suspension provided to the culture vessel at a temperature higher than the cloud point.

In the present invention, an aqueous solution of a temperature sensitive composition having a cloud point lower than the temperature of a clean room is prepared by adding 2-amino-2-hydroxymethyl-1,3-propanediol to an aqueous solution of a polymer material having 2-N,N-dimethylaminoethyl methacrylate (DMAEM) and/or a derivative thereof as the main polymer component. Nucleic acid is mixed into the aqueous solution of the temperature sensitive composition, and the resulting mixed liquid is adhered to the inner surface of the culture vessel. The mixed liquid becomes a gel at a temperature higher than the cloud point, forming a coating layer. As long as the temperature in the culture environment is equal to or greater than the cloud point of the temperature sensitive composition, the coating layer stably adheres to the surface of the culture vessel over an extended period of time. Furthermore, the temperature-sensitive polymer material in this coating layer includes cationic DMAEM units and can stably support a sufficient amount of nucleic acid.

In the present invention, the cation/anion ratio (C/A ratio) of the temperature-sensitive polymer material to the nucleic acid is from 1/0.7 to 1/1.2, and in particular is preferably from 1/0.8 to 1/1.1. By setting the C/A ratio of the temperature-sensitive polymer material to the nucleic acid to be within the above ranges, sufficient gene transfer activity can be achieved while suppressing hydrolysis of the DMAEM units.

Note that in the present invention, the C/A ratio refers to the ratio of the number of moles of cations of the temperature-sensitive polymer material (DMAEM units) to the number of moles of anions of the nucleic acid (phosphate residue).

In the present invention, the concentration of the temperature-sensitive polymer material in the gene transfer material is set from 0.001% to 1.0% by weight, in particular from 0.01% to 0.1% by weight, thereby allowing for uniform coating onto the culture vessel or the like.

In order to prepare the gene transfer material, nucleic acid is added to and mixed with an aqueous solution of a temperature sensitive composition at a temperature equal to or lower than the cloud point of the temperature sensitive composition, the temperature sensitive composition having 2-amino-2-hydroxymethyl-1,3-propanediol added therein to reduce the cloud point. The temperature-sensitive polymer material is thus caused to support the nucleic acid.

The type of aqueous medium used to prepare the aqueous solution of the gene transfer composition may be any aqueous medium well known to a person of ordinary skill in the art, such as a normal saline solution, water (ultrapure water or the like), phosphate buffer solution, HEPES buffer solution, carbonate buffer solution, Good buffer, or the like.

The gene transfer composition formed by mixing the aqueous solution of the temperature sensitive composition with nucleic acid is hydrophilic at a lower temperature than the cloud point of the temperature sensitive composition and is hydrophobic at a higher temperature than the cloud point.

With the aqueous solution of the gene transfer composition at a temperature lower than the cloud point, for example approximately 10° C. to 25° C., the aqueous solution is adhered to the culture vessel by casting, coating, or the like, raised to a temperature higher than 30° C. (such as 30° C. to 40° C.), and dried as necessary, thereby forming a water-insoluble coating layer supporting nucleic acid.

[Culture Vessel]

Examples of the culture vessel include a Petri dish, flask, culture plate (multiwell plate), and the like. The material thereof may be synthetic resin, glass, metal, or the like. When the gene transfer composition is adhered to the inner surface of the culture vessel, the gene transfer material is preferably adhered to the inner surface of the culture vessel to a density of approximately 0.7 ng/mm$^2$ to 70 μg/mm$^2$.

The method of adhering the gene transfer composition to the culture vessel is preferably a method to form a coating layer by first pipetting the gene transfer material into the culture vessel, subsequently causing the gene transfer material to adhere by casting the gene transfer material over the entire inner surface of the culture vessel while gently rolling the vessel side to side and up and down, and then incubating for approximately 1 to 360 minutes at 30° C. to 40° C. When adopting this method, drying may be performed in a sterile environment after the above-described incubation, or the coating layer may be formed by omitting the incubation and drying in a sterile environment.

As is well known to a person of ordinary skill in the art, an incubator for cell culturing is humidified in order to prevent the culture medium in the culture dish from vaporizing and becoming concentrated and to stabilize the carbon dioxide concentration in the incubator. When drying the gene transfer material adhered to the inner surface of the culture vessel, rapid drying is possible by temporarily suspending humidification of the incubator. Even when humidifying, the gene transfer composition is a small amount of liquid compared to the culture medium and therefore can be dried in approximately 24 hours (for example, when using a 24-well culture dish, the typical amount of culture medium is 1 mL, whereas approximately 150 μL of the gene transfer composition according to the present invention is added).

A suspension of mammalian cells is injected into the culture vessel and cultured at a temperature of approximately 37° C. to introduce nucleic acid into the cells. As a result, nucleic acid in the coating layer is incorporated into the cells. Note that with this method, it is thought that cells adhere to the coating layer and receptors in the cells gather on the coating layer side, so that nucleic acid is incorporated through the receptors.

[Nucleic Acid]

As the nucleic acid, it is possible to use various types of siRNA, antisense, or decoy; herpes simplex virus thymidine kinase gene (HSV1-TK gene); p53 tumor suppressor gene or BRCA1 tumor suppressor gene; TNF-α gene, IL-2 gene, IL-4 gene, HLA-B7/IL-2 gene, HLA-B7/B2M gene, IL-7 gene, GM-CSF gene, IFN-γ gene, IL-12 gene, or the like as a cytokine gene; and gp-100, MART-1, MAGE-1, or other cancer antigen peptide. It is also possible to use a cytokine gene such as a VEGF gene, HGF gene, FGF gene, or the like; or c-myc antisense, c-myb antisense, cdc2 kinase antisense, PCNA antisense, E2F decoy, or p21 (sdi-1) gene. It is also possible to use SOX2, c-Myc, OCT3, OCT4, Klf-4, NanoG, or the like.

The nucleic acid is used in a form allowing for expression of functionality within a cell by being introduced into the cell. For example, in the case of DNA, a plasmid containing the DNA is used to express functionality by the DNA being transcribed in the cell in which the DNA is introduced, so that the polypeptides coded therein are produced. Preferably, the promoter region, start codon, DNA coding a protein having the desired functionality, stop codon, and terminator region form a continuous sequence. As desired, two or more nucleic acids may be included in one plasmid.

[Application]

A coating layer of the gene transfer composition according to the present invention may be formed on the inner surface of a culture vessel, and after drying the coating layer, a different nucleic acid complex layer may be formed on top of the coating layer, thereby expanding the applications of the present invention.

To form the coating layer of the gene transfer composition, for example patterning may be performed by printing a predetermined pattern with an inkjet printer or the like and then drying as necessary. Accordingly, application to production of micro-arrays, DNA chips, or collections of cells of a different species, for example, is expected.

EXAMPLES

Examples are provided below to describe the present invention in greater detail. As long as the scope of the present invention is not exceeded, however, the present invention is not limited to the following examples.

Example 1 i) Synthesis by Photopolymerization of a Temperature-Sensitive Cationic Homopolymer 7.0 g of 2-(N,N-dimethylaminoethyl) methacrylate were added to a 50 mL transparent soft glass vial and mixed with a magnetic stirrer, and after purging for 10 minutes in high purity nitrogen gas, the result was exposed to ultraviolet light for 21 hours under a round, black fluorescent lamp. The result thickened in approximately 5 hours and hardened after 15 hours. The light-irradiated material was dissolved in chloroform and collected, a polymer was reprecipitated with n-hexane, and the polymer was purified by repeating reprecipitation 6 times with the chloroform/n-hexane system. After evaporating the n-hexane and dissolving in a small amount of benzene, the result was filtered with a 0.2 μm filter and freeze dried to yield a temperature-sensitive cationic homopolymer.

The number average molecular weight using polyethylene glycol as a standard substance was measured by GPC as 120,000 (Mw/Mn=2.4). Next, the measurement results of $^1$H-NMR (in CD$_3$OD) were δ0.8-1.2 ppm (br, 3H, —CH$_2$—CH$_3$—), δ1.6-2.0 ppm (br, 2H, —CH$_2$—CH$_3$—), δ2.2-2.4 ppm (br, 6H, N—CH$_3$), δ2.5-2.7 ppm (br, 2H, CH$_2$—N), δ4.0-4.2 ppm (br, 2H, O—CH$_2$).

ii) Measurement of the Cloud Point

An aqueous solution of 3% by weight ("%" referring to "% by weight" below) of the temperature sensitive cationic homopolymer (referred to below simply as "polymer") synthesized in i) (also referred to below simply as a "polymer solution") was prepared, and the temperature dependency of absorbance at 660 nm was measured from 20° C. to 40° C. Note that for the measurement in ii), an aqueous solution of suspended polymer at 40° C. was cooled to 20° C. at a rate of 1° C. per minute, and the cloud point was taken to be the temperature at which the solution became transparent. As a result, the cloud point was found to be near 32° C.

iii) Drop in Cloud Point

Measurement Example I on the Effect of adding Tris999

Granules of 2-amino-2-hydroxymethyl-1,3-propanediol (Tris999 made by Wako Pure Chemical, referred to as "Tris" below) were mixed with the polymer solution prepared in ii), and water was added to adjust the final concentration to a range of 1 mM to 1000 mM. The final concentration of the polymer was adjusted to a range of 0.01% to 2.5%.

At room temperature, the polymer solution started to be suspended at the moment the granules of Tris were mixed into the polymer solution. At a polymer concentration of 0.5% or more, the entire solution became a gel, and at a polymer concentration of less than 0.2%, agglomerated polymer lumps phase separated from water and precipitated. At a Tris concentration of less than 10 mM, agglomerated polymer lumps phase separated from water and precipitated, and at 100 mM or more, the entire solution became a gel. It is thought that the polymer material agglutinates easily due to polymer side chains and 2-amino-2-hydroxymethyl-1,3-propanediol molecules quantitatively forming cross-linking bonds. When both the polymer lumps that agglomerated/phase separated and the polymer lumps that formed a gel were transferred to a refrigerator, they quickly dissolved to yield a colorless, transparent aqueous solution, and when returned to room temperature, the solution was highly responsive, returning either to polymer lumps that agglomerated/phase separated or formed a gel. Even when this operation was repeated, responsiveness did not change, thus confirming the occurrence of a reversible phase transition phenomenon.

Table 1 shows the results of measuring the cloud point as in ii) above.

TABLE 1

| Tris concentration in mixed aqueous solution (mM/L) | Cloud point (° C.) |
| --- | --- |
| 0.0 | 32.2 |
| 1 | 32.2 |
| 10 | 25-28 |
| 50 | 20-25 |
| 100 | 10-25 |
| 300 | 10-20 |
| 500 | 10-20 |
| 1,000 | 10-20 | iv) Coating of Culture Dish and Gene Transfer

20 μg of DNA coding firefly luciferase (pGL3 control by Promega) was dissolved in 2000 μL of normal saline solution and stored at 4° C. 1580 μg of the polymer synthesized in i) above was dissolved in 500 μL of normal saline solution at 4° C. and referred to as liquid A. 1580 μg of Tris was dissolved in 500 μL of normal saline solution at 4° C. and referred to as liquid B. 300 μL each of liquid A and liquid B were mixed and stored at 4° C.

This mixed liquid was divided into 2 mL PCR tubes (DNase, pyrogen-free) in amounts of 6, 10, 14, 20, and 40 μL, and normal saline solution was added and mixed in amounts of 94, 90, 86, 80, and 60 μL. 100 μL of the DNA solution was added to each solution and mixed (the C/A ratios respectively being 3, 5, 7, 10, and 20), and 100 μL of the normal saline solution was further added to each solution and mixed. The solutions were sufficiently cooled at 4° C., and 300 μL (total amount) was added to each well in a 24-well culture dish and rapidly cast. During this casting operation, it was visually confirmed that the nucleic acid complexes became hydrophobized and deposited on the bottom of the culture dish. Furthermore, after insertion in a 37° C. incubator and incubation for 3 minutes, the culture dish was left standing for 15 minutes in a clean bench, and the liquid component in each well of the culture dish was removed by suction. This corresponds to how a person of ordinary skill in the art would leave the culture dish at room temperature for a sufficient time for a gene transfer operation in a clean bench and then remove the soluble component having an LCST of room temperature or less by suction.

Next, 1 mL each of a complete culture medium suspension (DMEM+10% FCS solution) of COS-1 cells, adjusted to a cell density of $5 \times 10^4$ cells/mL, was seeded into each well of the culture dish and cultured for 48 hours. After culturing for 48 hours, the culture medium was removed, 200 μL of a cell lysing agent was added to each well after washing twice with PBS, and the result was left at 4° C. for 30 minutes. Insoluble matter was precipitated by ultracentrifugation, and the supernatant was taken as a sample for gene transfer activity assessment. Gene transfer activity was assessed with a luciferase assay. For firefly luciferase activity, a luciferase assay kit by Promega was used, and normalization was performed with protein concentration. Protein was quantitatively determined with the Bradford reagent by BioRad. FIG. 1 shows the results.

As shown in FIG. 1, it is clear that genes were transferred from the bottom of the culture base material that was worked on at room temperature, left standing for 15 minutes, and on which suction removal was performed. These results confirm that the polymer material used in the present example fixes to the culture dish even at room temperature, without becoming removed or dissolving.

Comparative Example 1

An experiment was performed conforming to Example 1 in all respects other than using the polymer synthesized in i) above alone (i.e. mixing the polymer with an equal amount of normal saline solution, without mixing in Tris). First, a mixed solution of the polymer solution, nucleic acid, and normal saline solution was dripped into a 24-well culture dish, and after casting, was heated for 3 minutes at 37° C. Subsequently, the culture dish was returned to room temperature and left standing for 15 minutes, and suction removal was then performed.

After drying, the bottom of the well was observed, revealing that no solid content remained, with only a slight salt-like component on the outer periphery of the well.

After suction removal, the COS 1 cells were used to perform a gene transfer experiment, yet no significant difference from a blind value was observed for luciferase activity.

Comparative Example 2

After heating at 37° C. in Comparative Example 1, a cell suspension was added rapidly (so that the temperature would not drop), without removing liquid by suction, and the culture dish was immediately returned to 37° C. Gene transfer activity was then assessed. As a result, a coating of nucleic acid complexes was not formed. Furthermore, with a t-test no significant difference was observed from the value for transfer activity when mixing with a cell suspension and seeding a new culture dish. In either case, this was considered to be the result of nucleic acid complexes that decomposed and dissolved in the culture medium solution being incorporated into COS cells from the culture medium side.

Example 2

Figure 2:
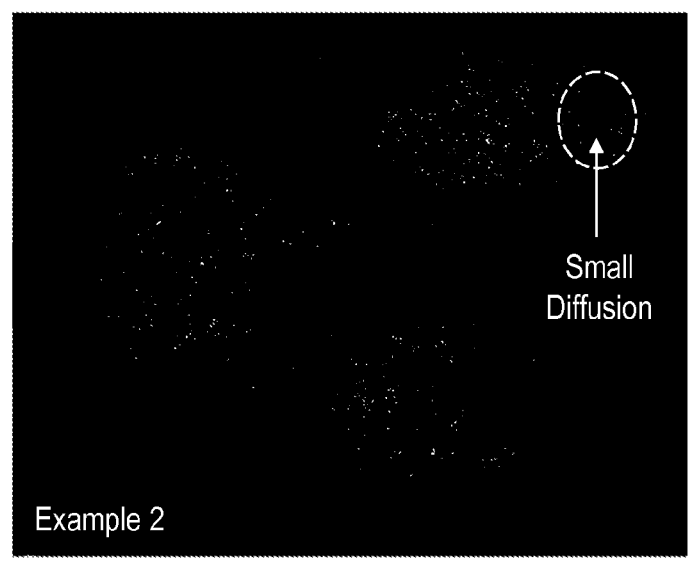
FIG. 2 is a GFP fluorescence microscopy photograph in Example 2 and Comparative Example 3.
Figure 2:
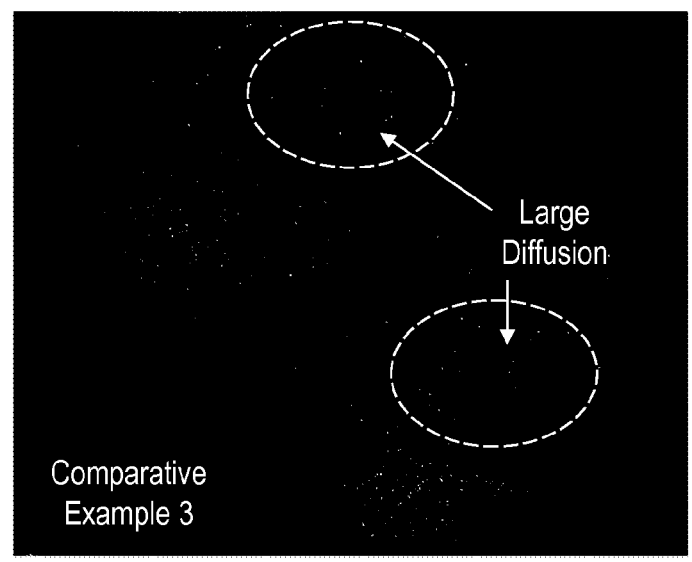

Gene transfer was performed in the same way as in Example 1, except that liquid A and liquid B were mixed so that Tris was 4 times the weight of the polymer, and instead of adding 200 μL of the cell lysing agent, drops of 20 μL of the cell lysing agent were adhered to the bottom of the culture dish partially, in a dot pattern. FIG. 2 shows a GFP fluorescence microscope image of the bottom of the culture dish for the resulting sample.

Comparative Example 3

Gene transfer was performed in the same way as in Example 2, except that the Tris liquid B was not mixed in. FIG. 2 shows a GFP fluorescence microscope image.

As is clear from FIG. 2, in Example 2, the GFP gene was expressed just as in the dot pattern, and the emission of green fluorescent light was confirmed. These results show that the GFP gene is not expressed in portions other than where the nucleic acid complexes were adhered, thus allowing for pattering control. In other words, a target gene can be transferred exclusively to a target portion. This technique can be considered, for example, to demonstrate the ability to use an inkjet printer or the like to print a plurality of nucleic acid complex solutions as desired (and localizing by heating) to form a cell layer having a variety of genes transferred therein, only in controlled portions.

Example 3

Gene transfer was performed in the same way as in Example 1, except that liquid A and liquid B were mixed so that Tris was 4 times the weight of the polymer, and without humidifying, incubation was performed at 37° C. for 24 hours to dry the solution. Gene transfer activity was assessed similarly, revealing that gene transfer activity was approximately 100 times that of Example 1, which does not include a drying step.

In the gene transfer experiment disclosed in JP 2006-131591 A and with a conventional method in which nucleic acid complexes are dried, gene transfer is not expressed even when freeze drying, whereas with the present invention, drying instead increases the gene transfer activity.

One reason for obtaining this effect is that in a conventional method in which nucleic acid complexes are incorporated into cells as 100 nm to 200 nm fine particles, upon including the drying step, the nucleic acid complexes become macroparticles (i.e. increase to a size that cannot be incorporated into cells) due to decomposition of genes and agglomeration of fine particles. In the present invention, on the other hand, gene transfer is from the solid phase to begin with, and even without drying, genes are incorporated into cells from the layer of agglomerated polymer. Therefore, drying does not cause deactivation. While the reason for a 100 fold increase in activity as compared to the case of not drying is uncertain, it is thought that genes more easily come free from the agglomerated layer.

[Measurement Example II on the Effect of Adding Tris]

The polymer synthesized in i) of Example 1 and Tris were dissolved in water. The final concentration was adjusted to 0.1% polymer, and the ratio by weight of Tris to the polymer was adjusted to 0, 0.5, 1.0, 2.0, 4.0, and 8.0. Note that 0 indicates that Tris was not added.

2 mL of each aqueous solution was placed in a 10 mm by 10 mm square quartz cell (1 mm thick) and made cloudy by heating in a 37° C. water bath.

Figure 3:
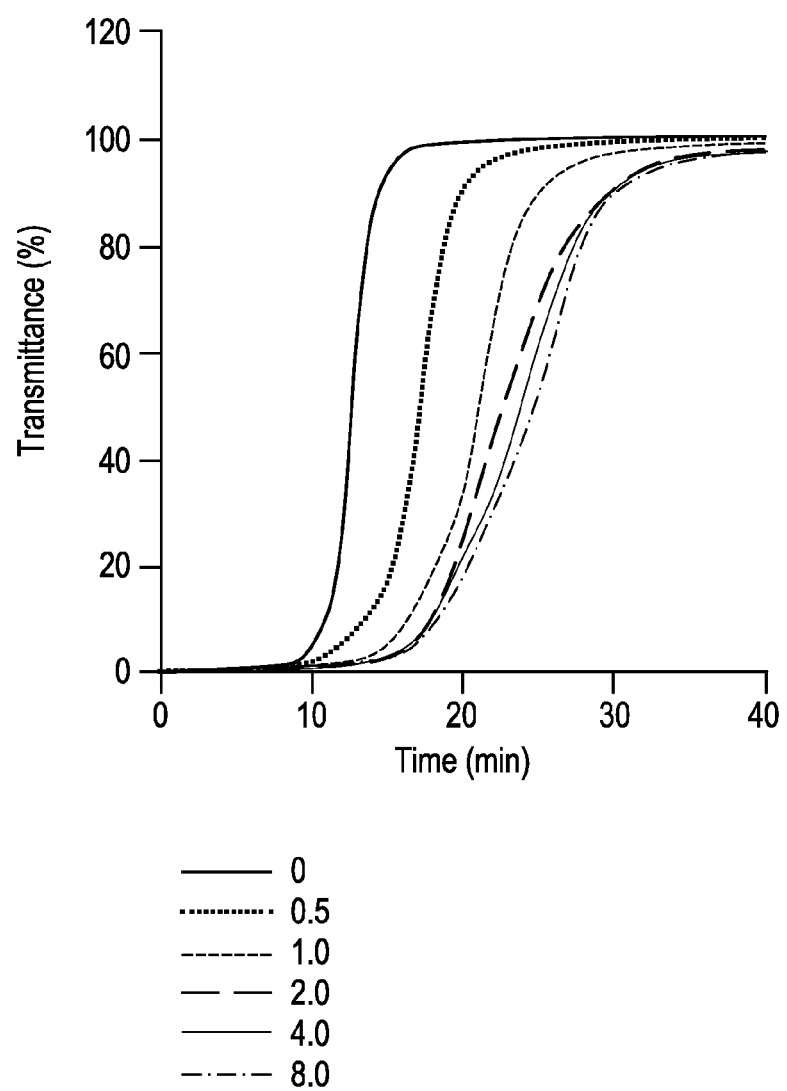
FIG. 3 is a graph showing the change over time of transmittance in the Examples.

Each cell was set in an absorption spectrometer installed in a temperature-controlled room at 25° C., and the change over time of transmittance at a wavelength of 600 nm was measured. FIG. 3 shows the results.

As illustrated in FIG. 3, as the added amount of Tris increased, the time for the cloudy solution to become transparent grew longer. The reason is considered to be that as the added amount of Tris increases, the polymer material agglutinates more easily. In the experiment in iii) above, assessment is made by measuring the temperature when the agglutinated polymer solution rapidly becomes transparent in a temperature environment at or above the cloud point. In the experiment in this section, <Measurement Example II on the effect of adding Tris>, assessment is made by measuring the time until dissolving when the agglutinated polymer is maintained at a temperature of 25° C. While either can be considered the "cloud point", it is clear that differences occur depending on the method of measurement.

[Measurement Example III on the Effect of Adding Tris]

The polymer synthesized in i) of Example 1 and Tris were dissolved in water. The final concentration was adjusted to 0.1% polymer, and the ratio by weight of Tris to the polymer was adjusted to 0, 0.5, 1.0, 2.0, 4.0, and 8.0. Note that 0 indicates that Tris was not added.

2 mL of each aqueous solution was placed in a 10 mm by 10 mm square quartz cell (1 mm thick).

Each cell was set in an absorption spectrometer installed in a temperature-controlled room at 20° C., and the transmittance at a wavelength of 600 nm was measured after 40 minutes had elapsed.

Measurement was the same as above, except that the temperature was set to 21° C., 22° C., . . . , and 37° C. (increments of 1° C.). Table 2 shows the results.

Note that from the results of the experiment in the above Measurement Example II on the effect of adding Tris, it is clear that when the temperature of the aqueous solution is maintained constant, the state of the polymer stabilizes after approximately 30 to 40 minutes. Therefore, it can be said that the measurement value in the experiment for this Measurement Example III on the effect of adding Tris is the "cloud point" that is not easily affected by external factors.

TABLE 2

| Tris/polymer (ratio by weight) | Cloud point (° C.) |
| --- | --- |
| 0 | 32 |
| 0.5 | 31 |
| 1.0 | 30 |
| 2.0 | 29 |
| 4.0 | 29 |
| 8.0 | 29 |

As shown in Table 2, it was confirmed that the cloud point of the polymer is 32° C., that the cloud point lowers by adding Tris, and that there is a loose correlation between the addition of Tris and the amount by which the cloud point lowers.

[Measurement Example IV on the Effect of Adding Tris]

The polymer synthesized in i) of Example 1 and Tris were dissolved in water. The final concentration was adjusted to 0.1% polymer, and the ratio by weight of Tris to the polymer was adjusted to 0.65, 1.3, 2.6, and 5.8.

Figure 4:
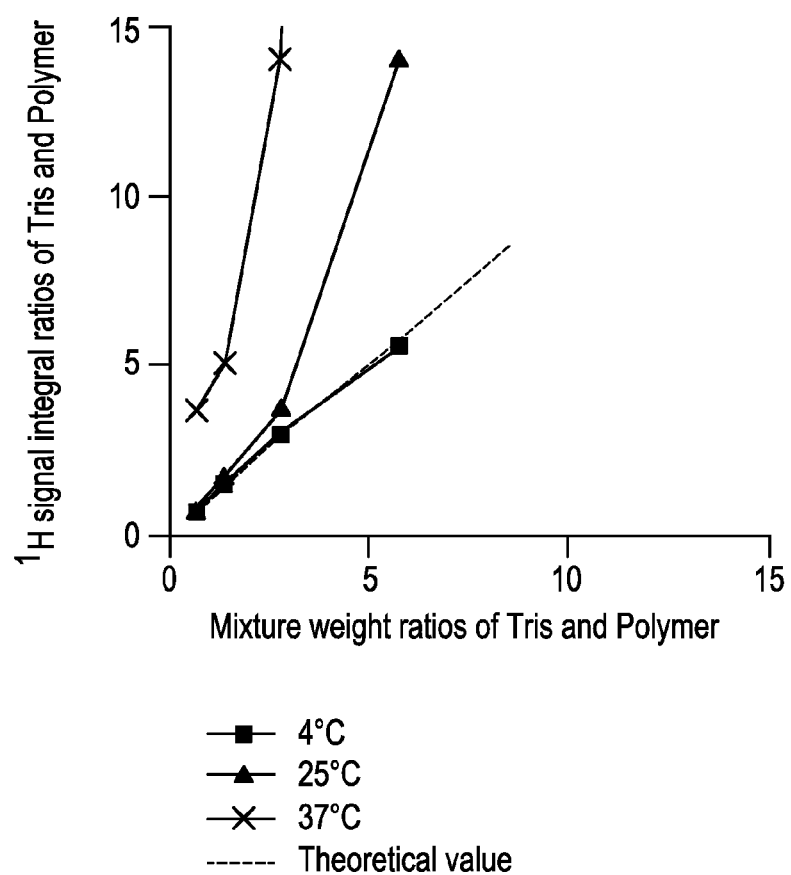
FIG. 4 is a graph showing the results obtained by NMR measurement for the Examples.

For each Tris/polymer solution, NMR measurement was performed at the temperatures of 4° C., 25° C., and 37° C., and the ratio of the $^1$H integral of —N(CH$_3$)$_2$ in the polymer side chain to the $^1$H integral of —CH$_2$— in the Tris was calculated. FIG. 4 shows the results.

As is clear from FIG. 4, the ratio of the $^1$H integral of —N(CH$_3$)$_2$ in the polymer side chain to the $^1$H integral of —CH$_2$— in the Tris is the same as the compounding ratio at 4° C., yet at 25° C., the ratio deviates from the theoretical value in a region where the added amount of Tris is large, and at 37° C., the peak of the polymer side chain is not detected.

This is considered to be the result of shielding by micelle formations due to hydrophobic agglomerations.

[Measurement Example V on the effect of adding Tris]

The polymer synthesized in i) of Example 1 and Tris were dissolved in water. The final concentration was adjusted to 0.1% polymer, and the ratio by weight of Tris to the polymer was adjusted to 0, 0.5, 1.0, 2.0, 4.0, and 8.0. Note that 0 indicates that Tris was not added.

Figure 5:
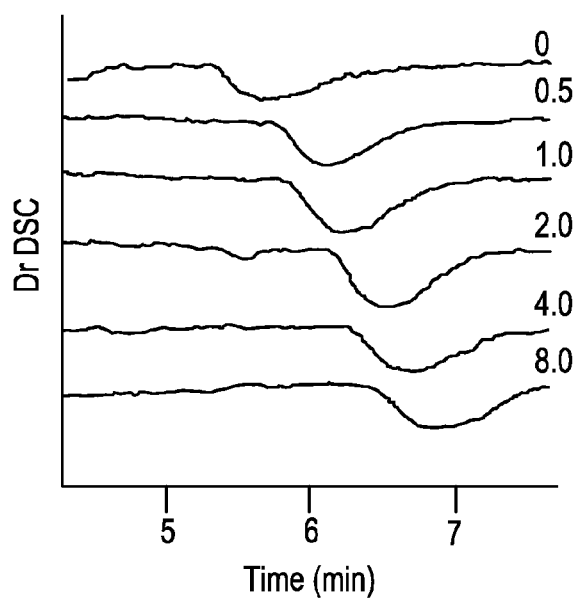
FIG. 5 is a graph showing the results obtained by DSC measurement for the Examples.

For each Tris/polymer solution, the DSC curve when the solution was solidified at 40° C. and then instantaneously cooled to and maintained at 25° C. was measured. FIG. 5 shows the results. FIG. 5 shows that along with an increase in the compounded amount of Tris, the time until the absorption of heat (until the hydrophobic agglomeration dissolves) is prolonged.

[Measurement Example VI on the effect of adding Tris]

The polymer synthesized in i) of Example 1 and Tris were dissolved in water. The final concentration was adjusted to 30% polymer, and the ratio by weight of Tris to the polymer was adjusted to 0, 0.5, and 2.0. Note that 0 indicates that Tris was not added.

The present measurement was performed at 20 times the concentration of the gene transfer experiment due to the IR detection sensitivity.

Polystyrene Petri dishes for cell culturing were cut to a size of 20 mm by 50 mm, 100 µL each of the Tris/polymer solutions were dripped therein, and the Petri dishes were incubated for 6 hours at 37° C. while being humidified. Subsequently, after removing the solution by suction at room temperature, humidification was stopped, and the Petri dishes were dried for 24 hours in an incubator at 37° C.

The infrared absorption spectrum was measured by ATR to investigate the dependence on Tris concentration of the polymer remaining on the base material surface.

Figure 6:
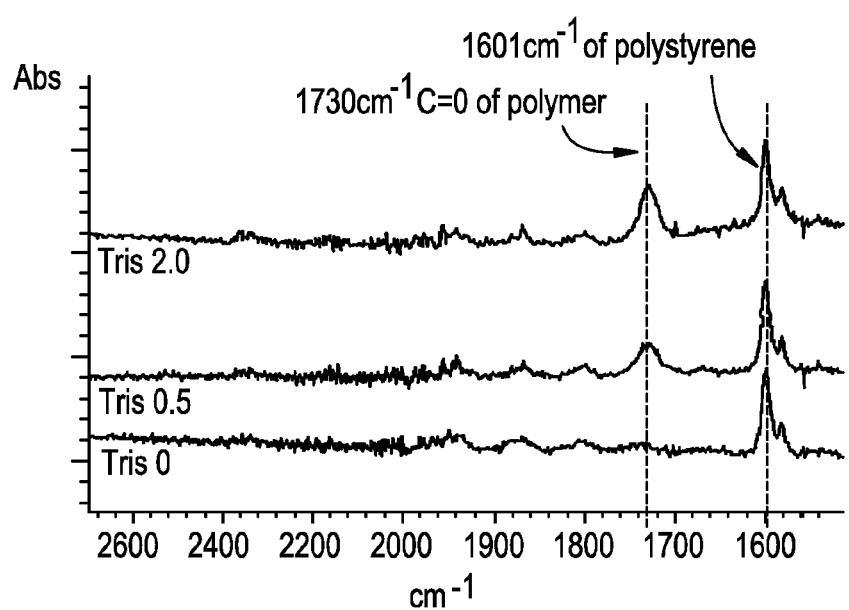
FIG. 6 is a chart showing the results obtained by IR measurement for the Examples.

As shown in FIG. 6, the results for the ratio of the 1730 $cm^{-1}$ absorption derived from C=O for the polymer to the 1601 $cm^{-1}$ absorption derived from the polystyrene of the Petri dish were as follows: Tris 0=0.00, Tris 0.5=0.45, and Tris 2.0=0.62, thus showing that the polymer remaining on the polystyrene base material surface depended on the concentration of the added Tris.

[Observations]

From the results of four measurement examples based on different principles, namely Measurement Example II: transmittance by agglomeration in water (cloudy), Measurement Example IV: magnetic field shielding by hydrophobic agglomeration in water, Measurement Example V: change in heat energy upon becoming soluble again, and Measurement Example VI: infrared absorption, it was confirmed that by compounding Tris, the thermal responsiveness of the Tris/polymer composition changed.

From this result, it is clear that according to the present invention, compounding Tris can achieve the effects of preventing the polymer coating layer from being eluted during operation at 25° C. and of sufficiently achieving the purpose of the agglutinated layer formed to be temperature sensitive.

Example 4

A gene coding GFP (pQB125 by TAKARA Biomedicals) was dissolved in a normal saline solution to a concentration of 1 µg/30 µL and stored at 4° C. The polymer synthesized in i) of Example 1 was dissolved in normal saline solution at 4° C. to a concentration of 4 µg/30 µL and referred to as liquid C. 1580 µg of Tris was dissolved in 500 µL of normal saline solution at 4° C. and referred to as liquid D. 300 µL each of liquid C and liquid D were mixed and stored at 4° C.

This mixed liquid was divided into 2 mL PCR tubes (DNase, pyrogen-free) in amounts of 3.8, 7.5, 15, and 30 µL, and normal saline solution was added and mixed in amounts of 96.2, 92.5, 85, and 70 µL. 50 µL of GFP gene solution were added and mixed into each solution. The C/A ratios were respectively 1, 2, 4, and 8. The solution was sufficiently cooled at 4° C., and 150 µL was added to each well in a 24-well culture dish and rapidly cast. The culture dish was then incubated for 6 hours in an incubator at 37° C.

Figure 7:
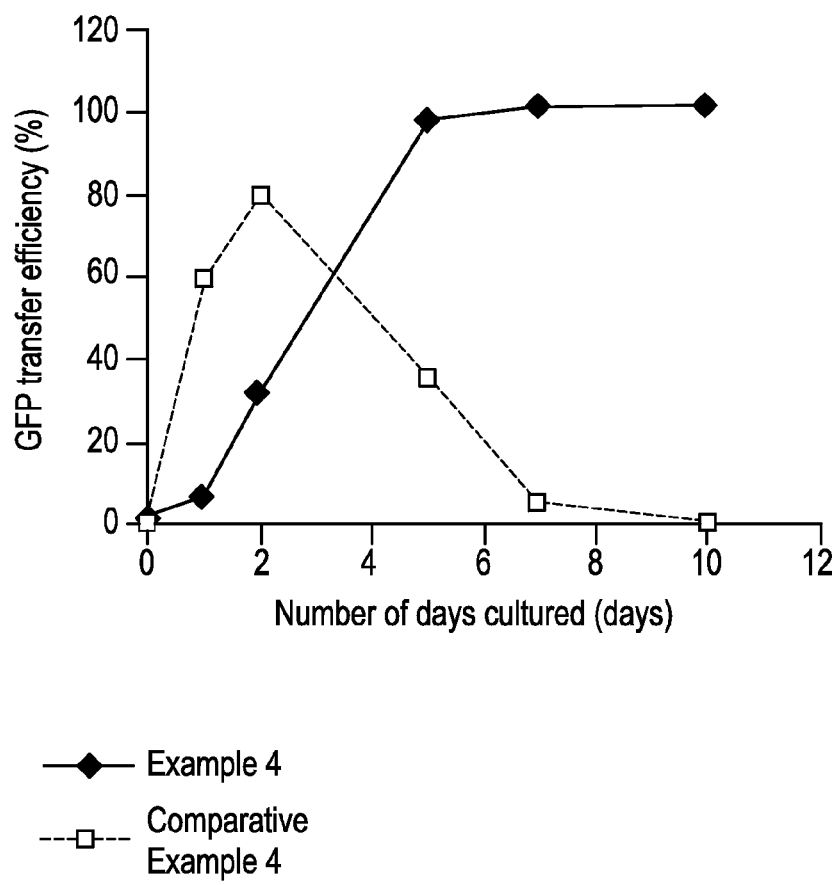
FIG. 7 is a GFP fluorescence microscopy photograph in Example 4 and Comparative Example 4.

Next, 1 mL each of a complete culture medium suspension (DMEM+10% FCS solution) of Hela cells, adjusted to a cell density of $7 \times 10^4$ cells/mL, was seeded into each well of the culture dish and cultured for 10 days. The gene transfer activity was assessed by fluorescence microscope observation. FIG. 7 shows the results.

Comparative Example 4

An experiment was performed in a similar way to Example 4, except that Lipofectamine 2000 (by Invitrogen) was used instead of a mixed solution of liquid C and liquid D. FIG. 7 shows the results.

As shown in FIG. 7, in Comparative Example 4 the expression of GFP fluorescence was confirmed from day 1, with expression reaching a peak on day 2. Thereafter, GFP fluorescence rapidly dimmed, until almost no expression could be confirmed on day 7. This is considered to be because when the nucleic acid complex solution was added, GFP fluorescence was expressed only by the cells that incorporated the nucleic acid (and some divided cells that inherited the nucleic acid), yet when the DNA (mRNA) in the cells was consumed or decomposed, GFP fluorescence was no longer expressed. By contrast, in Example 4, almost no expression of GFP fluorescence was confirmed on day 1, and approximately 1.5 days were required until GFP fluorescence could be confirmed. Thereafter, the rate of expression of GFP fluorescence increased, reaching a peak on day 5 and climbing to a rate of expression approximately 10 times that of the comparative example. In Example 4, this high rate of expression was maintained, and even on day 7 (and up to day 10) the light did not dim. In Example 4, the DNA or DNA complexes were released slowly over time from the bottom of the culture dish. Therefore, while the peak for expression of GFP fluorescence was approximately day 5 or later, high expression was maintained. This can be considered the result of how, due to the slow-release effect, the cells that increased by division as well as the cells that incorporated the DNA once and then consumed or decomposed the DNA were given the chance to incorporate DNA complexes. In addition to the above-described effect, such slow release achieves the following effects (i) and (ii).

(i) Gene transfer with a conventional method normally requires that the timing for providing nucleic acid be aligned with the mitotic phase of the cells (in other words, the opportunity for introduction is provided to cells for which the timing is aligned), whereas providing nucleic acid over an extended period of time allows for uniform provision of the opportunity for introduction into many cells anywhere in the cell cycle.

(ii) Slow release is also useful for introduction into cells with a low growth rate.

A commercial cytotoxicity assessment kit (WST-8 by Dojindo) was used to assess cytotoxicity for the cells after gene transfer in Example 4 and Comparative Example 4. As a result, the survival rate was 100% for Example 4 and approximately 80% for Conventional Example 4. A difference in cytotoxicity was thus confirmed between a conventional method for providing nucleic acid that damages the cell membrane of a large quantity of cells at once (Comparative Example 4) and Example 4, in which nucleic acid is provided incrementally over time. In other words, in addition to being useful for gene transfer, the slow-release effect in the gene transfer composition according to the present invention is clearly useful with respect to cytotoxicity.

The present invention has been described by a specific embodiment, yet a variety of modifications within the scope and spirit of the present invention will be apparent to a person of ordinary skill in the art.

This application claims priority to and the benefit of Japanese Patent Application No. 2011-287594 filed Dec. 28, 2011, the entire contents of which are incorporated herein by reference.

The invention claimed is:

1. A method for producing a cell having nucleic acid introduced therein, comprising the steps of:
    producing a gene transfer composition by mixing a nucleic acid with an aqueous solution of a temperature sensitive composition at a temperature less than 32° C., the temperature sensitive composition being formed by adding 2-amino-2-hydroxymethyl-1,3-propanediol to a temperature-sensitive polymer material having 2-N,N-dimethylaminoethyl methacrylate as a main polymer component;

adhering the gene transfer composition to a culture vessel; and culturing a cell suspension provided to the culture vessel at a temperature higher than 32° C. to give a cell comprising the nucleic acid within it.

2. The method for producing a cell having nucleic acid introduced therein according to claim 1, further comprising the step of drying the temperature sensitive composition between the step of adhering and the step of culturing.

3. The method for producing a cell having a nucleic acid introduced therein according to claim 1, wherein a molecular weight of the temperature sensitive polymer material is from 5,000 to 500,000.

* * * * *